(12) United States Patent
Smith et al.

(10) Patent No.: US 6,360,884 B1
(45) Date of Patent: Mar. 26, 2002

(54) TOOTHBRUSH STORAGE CONTAINER

(76) Inventors: Robert James Smith; Phyllis Clara Smith, both of 420 Planett St., Laporte, IN (US) 46350

( * ) Notice: Subject to any disclaimer, the term of this patent is extended or adjusted under 35 U.S.C. 154(b) by 0 days.

(21) Appl. No.: 09/628,894

(22) Filed: Jul. 31, 2000

(51) Int. Cl.[7] ............................................. B65D 85/00
(52) U.S. Cl. ................. 206/209.1; 220/23.4; 206/362.1
(58) Field of Search ............................ 206/209, 209.1, 206/362, 362.1, 362.2, 362.3; 220/23.4, 254, 811

(56) References Cited

U.S. PATENT DOCUMENTS

| | | | |
|---|---|---|---|
| 1,562,348 A | 11/1925 | Lockery | |
| 3,904,362 A | 9/1975 | DiPaolo | 21/87 |
| 4,585,119 A | 4/1986 | Boyington | 206/209.1 |
| 4,656,840 A | * 4/1987 | Loofbourrow et al. | 220/23.4 |
| 4,728,234 A | * 3/1988 | Reynard | 220/23.4 |
| 4,886,239 A | * 12/1989 | Stimmel | 220/23.4 |
| 4,893,719 A | * 1/1990 | Lombardi et al. | 220/23.4 |
| 4,915,219 A | 4/1990 | Ottimo | 206/209.1 |
| 4,919,296 A | * 4/1990 | Kirsh et al. | 220/23.4 |
| D322,732 S | 12/1991 | Stabe | D6/528 |
| 5,522,497 A | * 6/1996 | Stacy | 206/209.1 |
| 5,566,823 A | 10/1996 | Summers | 206/209.1 |
| 5,890,613 A | * 4/1999 | Williams | 220/23.4 |

* cited by examiner

Primary Examiner—Jim Foster

(57) ABSTRACT

A container for sanitary storage of a toothbrush is disclosed having a base, a compartment, a lid base and a lid hingedly connected to the lid base. The container can be interconnected with other like containers for added stability. The compartment has two female receptacles on the right side and two female receptacles on the left side for receiving connector plugs. The container may be adapted to different sized toothbrushes by insertion of a filler block. The container may be optionally mounted on the wall.

8 Claims, 3 Drawing Sheets

TOOTHBRUSH STORAGE CONTAINER

BACKGROUND OF THE INVENTION

1. Field of the Invention

The present invention relates to an apparatus for storing toothbrushes in a sanitary container while also allowing the containers to be interlocked.

2. Description of the Prior Art

The prior art discloses a variety of devices for sanitary storage of toothbrushes. U.S. Pat. No. 3,904,362 discloses a toothbrush holder having a compartmentalized body and individual toothbrush holders to immerse the toothbrush bristles in an antiseptic fluid. U.S. Pat. No. 5,566,823 discloses a container with a cap having a removable tray with separate compartments for insertion of toothbrush bristles into an antiseptic fluid. U.S. Pat. No. 4,585,119 (the '119 Patent) discloses elongated tubular containers with a necked down portion for holding a toothbrush in an antiseptic fluid. A holder uses flexible retaining devices that engage the necked down portion of the containers to secure the containers. The '119 patent also discloses caps for the containers. U.S. Pat. No. 4,915,219 discloses a container having a plurality of interior compartments for receiving the bristles of a plurality of toothbrushes in an antiseptic fluid. U.S. Pat. No. 1,562,348 (the '348 patent) discloses an individual toothbrush container using a spring or a float to keep the end of the toothbrush accessible at the top of the container. The '348 patent discloses an embodiment in which the toothbrush is kept in one compartment and the antiseptic fluid in another compartment.

What is needed beyond the prior art is a simple container for storage of a toothbrush in an antiseptic fluid which is simple, stable and easily positioned near a sink. Additionally, the container should be capable of interlocking with like containers so that each family member can have a separate container for his or her toothbrush. The container should be capable of containing an antiseptic fluid and capable of being closed when the toothbrush is not in use.

SUMMARY OF THE INVENTION

The present invention meets the needs and solves the problems identified above by providing a container having a base, a compartment, a lid base and a lid hingedly connected to the lid base. The container can be interconnected with other like containers for added stability. The compartment has two female receptacles on the right side and two female receptacles on the left side for receiving connector plugs. The container may be adapted to different sized toothbrushes by insertion of a filler block. The container may be optionally mounted on the wall.

The foregoing and other objects, features and advantages of the invention will be apparent from the following more particular description of a preferred embodiment of the invention, as illustrated in the accompanying drawings wherein like reference numbers represent like parts of the invention.

DESCRIPTION OF PREFERRED EMBODIMENTS

Figure 1:
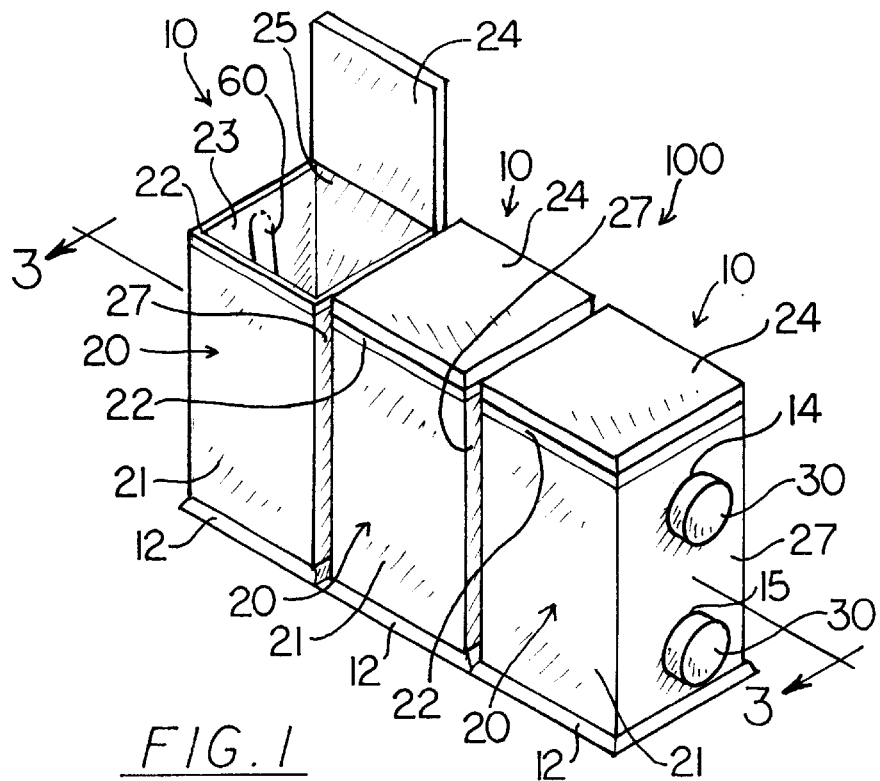
FIG. 1 is a right side perspective of three containers.

FIG. 1 depicts container assembly 100 having three containers 10 interconnected. Each container 10 is constructed in the same manner and with the same dimensions. However, each container 10 may be a different color or combination of colors to aid in identifying the toothbrush stored. Container 10 has base 12 removably connected to compartment 20. Compartment 20 is removably connected to lid base 22 and lid base 22 is hingedly connected to lid 24. In the preferred embodiment, compartment 20 is square with each side being approximately 1½ inches wide and having a height of approximately 9 inches. Compartment 20 front wall 21, right wall 27, left wall 23 and rear wall 25 and bottom 26 (see FIGS. 3a and 3b). Front wall 21, right wall 27, left wall 23, rear wall 25 and bottom 26 may be molded from one piece of plastic or other suitable material. Alternatively, front wall 21, right wall 27, left wall 23, rear wall 25 and bottom 26 may be made from separate pieces and joined so that compartment 20 is watertight. Lid base 22 is removably affixed to front wall 21, right wall 27, left wall 23 and rear wall 25. In the preferred embodiment, lid base 22 frictionally engages a lip (not shown) on top of front wall 21, right wall 27, left wall 23 and rear wall 25 so that lid base 22 may be removed from compartment 20 for cleaning or replacement. Lid 24 is hingedly connected to lid base 22 so that lid 24 rotates about an axis parallel to rear wall 25. In the preferred embodiment, base 12 is square and made of rubber or other suitable material. Base 12 is removably affixed to compartment 20. In the preferred embodiment, base 12 has a indented top surface for receiving the bottom of compartment 20. Compartment 20 has a top right receptacle 14 and a bottom right receptacle 15 for receiving plugs 30. Compartment 20 also has a top left receptacle 16 and a bottom left receptacle 17 for receiving plugs 30 (See FIG. 2). In leftmost compartment 20, lid 24 is open and toothbrush 60 is visible inside compartment 20. In an alternative embodiment, container 10 may be cylindrical and base 12 would be circular and lid base 22 and lid 24 would be circular.

Figure 2:
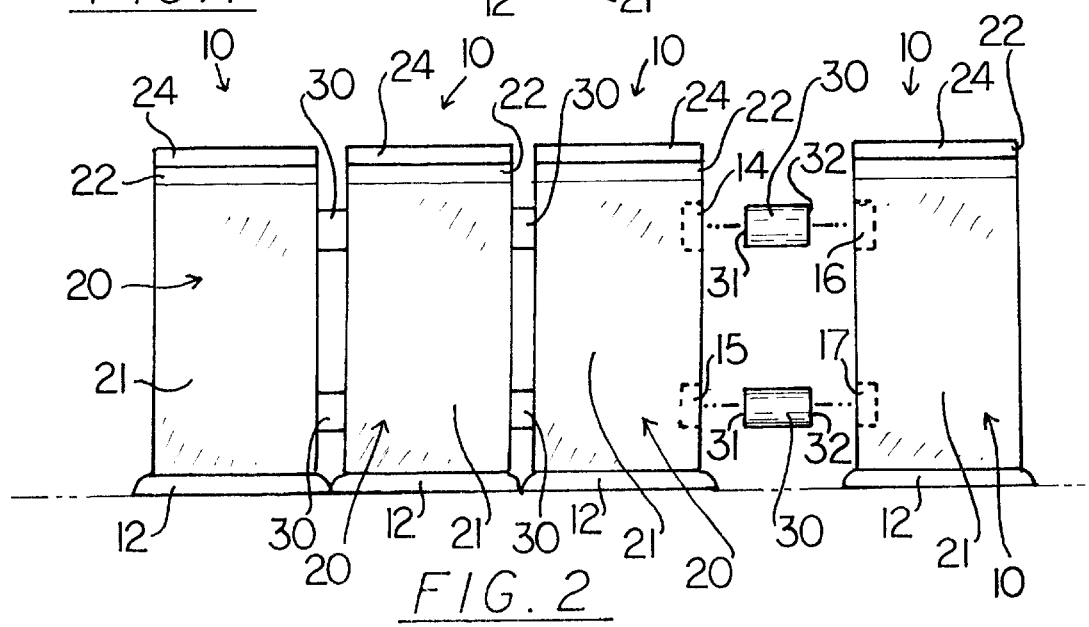
FIG. 2 is a front view of three connected containers with detail showing the addition of a fourth container.

FIG. 2 shows three containers 10 interconnected and a fourth container 10 about to be connected by connecting compartments 20. Compartments 20 are connected by inserting first end 31 of plug 30 into top right receptacle 14 and first end 31 of another plug 30 into bottom right receptacle 15. The top left receptacle of the non-connected compartment 20 is then engaged with second end 32 of plug 30 and bottom left receptacle of the non-connected compartment is then engaged with second end 32 of plug 30 and the fourth compartment 20 is now engaged in one unit with the first three compartments 20. Plugs 30 can be seen joining the three connected compartments 20.

Figure 3A:
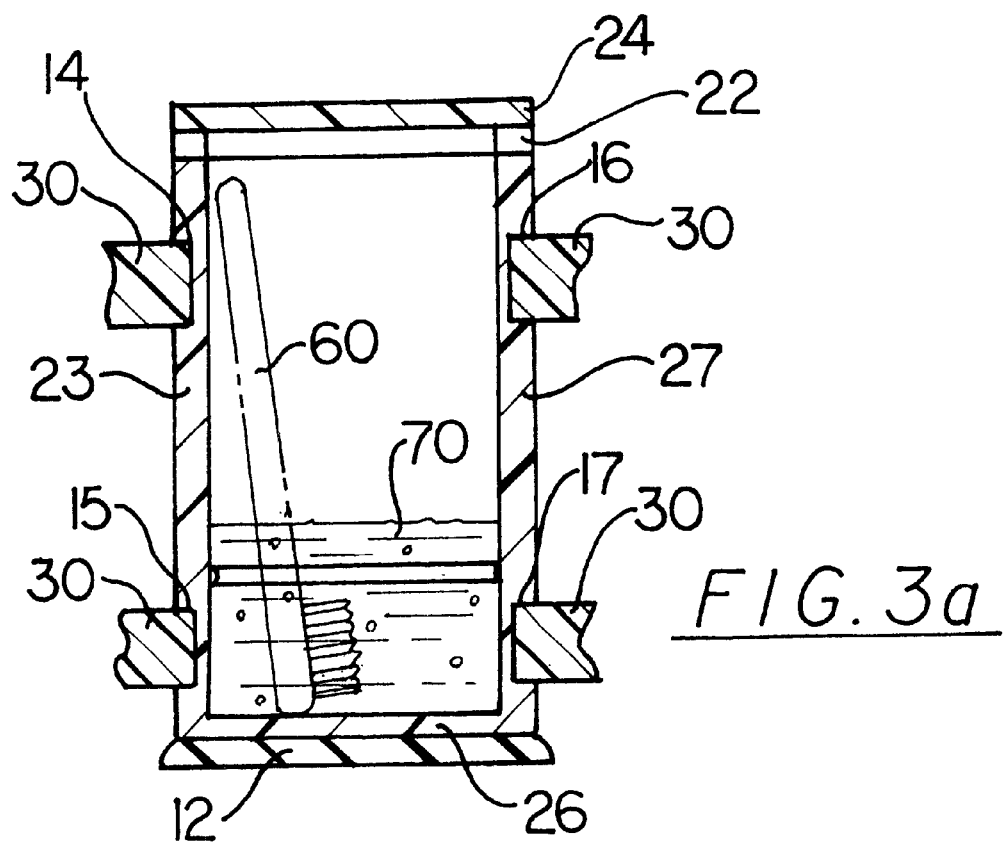
FIG. 3a is a cross sectional view along line 3—3 of FIG. 1 of a single container.

FIG. 3a is a cross sectional view along line 3—3 of FIG. 1 showing compartment 20 with first toothbrush 60 immersed in antiseptic fluid 70. The purpose of antiseptic fluid 70 is to sterilize and/or sanitize a toothbrush stored in compartment 20.

Figure 3B:
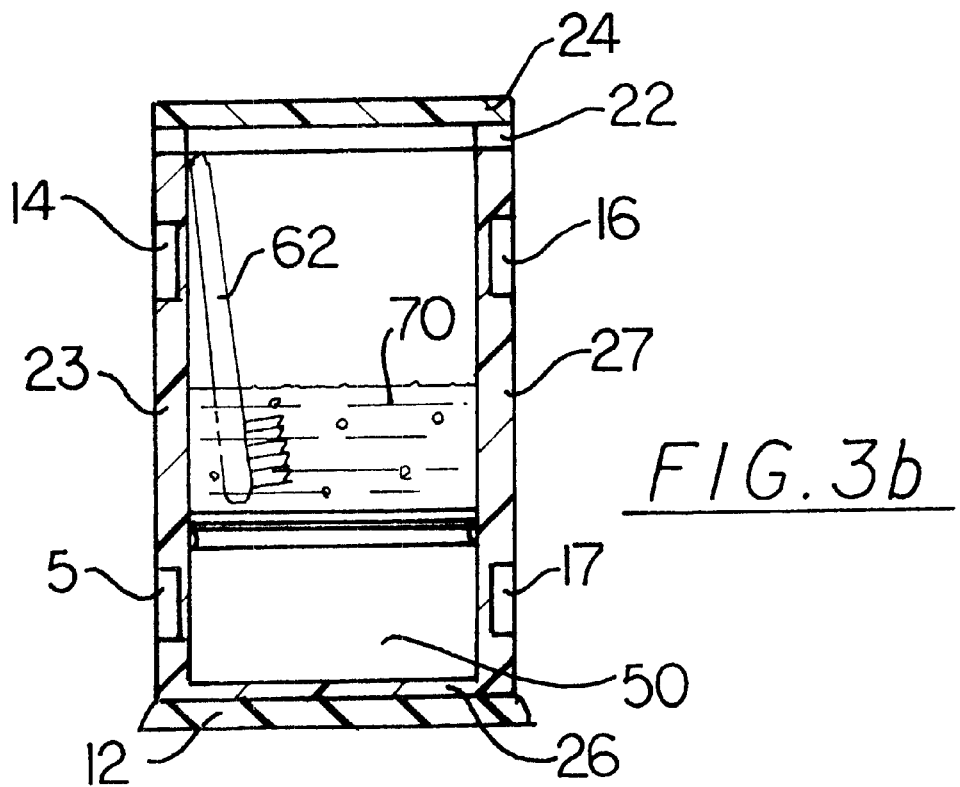
FIG. 3b is a cross sectional view along line 3—3 of FIG. 1 of a single container with a filler block inserted.

FIG. 3b shows second toothbrush 62 immersed in antiseptic fluid 70. Filler block 50 has been inserted into compartment 20 in order to raise the level of antiseptic fluid 70 for second toothbrush 62. Second toothbrush 62 is shorter than toothbrush 60 shown in FIG. 3a. Filler block 50 further allows access to second toothbrush 62 because the end of toothbrush 62 is near the top of compartment 20. Top right receptacle 16, bottom right receptacle 17, top left receptacle 14 and bottom left receptacle 15 are shown in FIG. 3b without inserted plugs 30.

Figure 4:
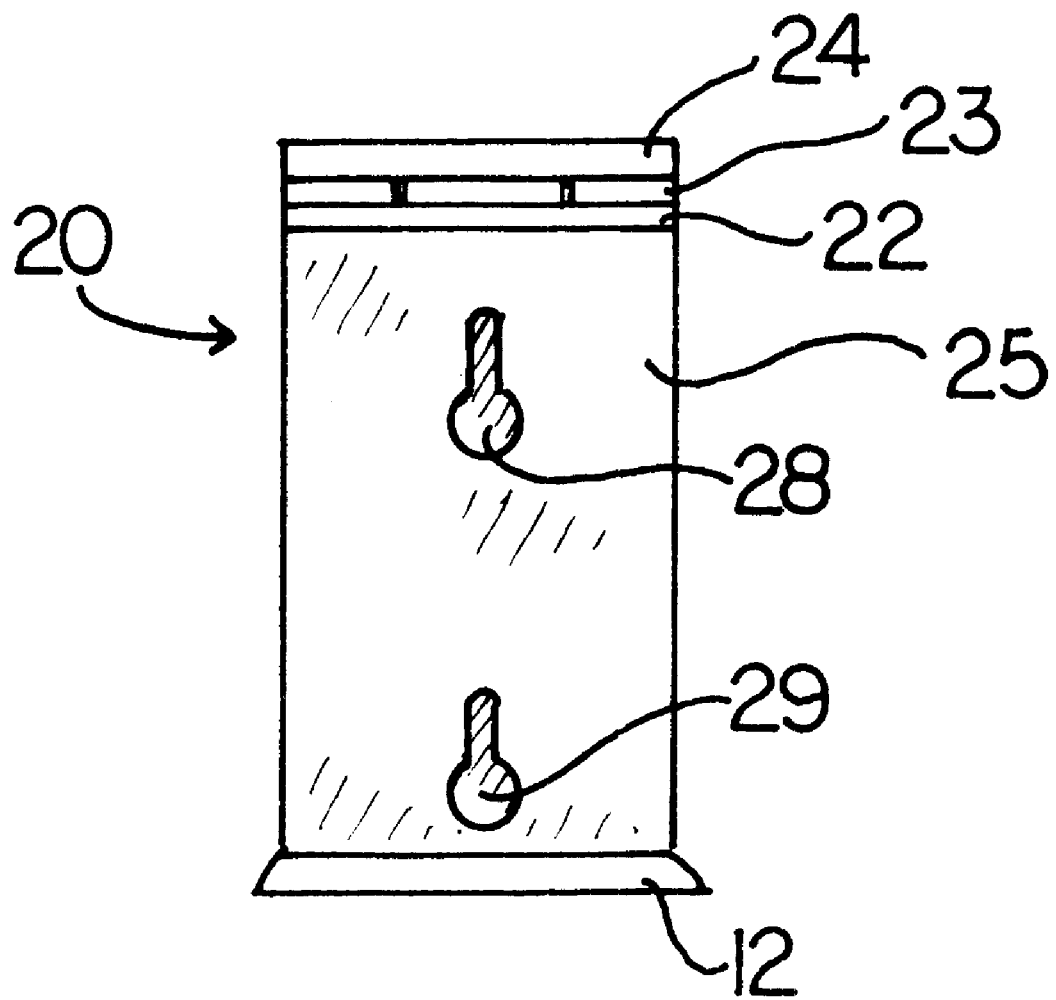
FIG. 4 is a rear view of a container.

FIG. 4 depicts a rear view of compartment 20 showing base 12, lid base 22, lid 24 and hinge 22 connecting lid base 22 and lid 24. Rear wall 25 of compartment 20 has first wall mounting aperture 28 and second wall mounting aperture 29 for optional mounting of compartment 20 of container 10 on a wall.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

We claim:

1. A container assembly for storage of a toothbrush comprising:
   a base;
   a compartment having a front wall, a rear wall, a right wall and a left wall;
   a lid assembly having a lid base removably connected to said compartment and a lid hingedly connected to said lid base;
   a top right receptacle and a bottom right receptacle located in said right wall; and
   a top left receptacle and a bottom left receptacle located in said left wall.

2. The container of claim 1 further comprising a filler block.

3. The container of claim 1 further comprising an antiseptic fluid.

4. A container assembly for storage of a toothbrush comprising:
   a base;
   a cylinder having an outer wall and an inner wall;
   a lid assembly having a lid base removably connected to said cylinder and a lid hingedly connected to said lid base;
   a top right receptacle and a bottom right receptacle located in said cylinder; and
   a top left receptacle and a bottom left receptacle located in said cylinder.

5. The container of claim 1 further comprising a filler block.

6. The container of claim 1 further comprising an antiseptic fluid.

7. A toothbrush storage system comprising:
   a first compartment and a second compartment;
   a first base connected to said first compartment and a second base connected to said second compartment;
   a lid assembly having a lid base removably connected to said first compartment and said second compartment and a lid hingedly connected to said lid base, a top right receptacle and a bottom right receptacle located in said first compartment and said second compartment, and a top left receptacle and a bottom left receptacle located in said first compartment and said second compartment; and
   a first plug and a second plug, each having a first end and a second end;
   wherein the first ends of said first plug and said second plug are inserted into the top right receptacle and the bottom right receptacle of said first compartment and the second ends of said first plug and said second plug are inserted into the top left receptacle and the bottom left receptacle of the second compartment thereby interconnecting said first compartment and said second compartment.

8. The toothbrush container system of claim 7 further comprising a filler block.

* * * * *